Feb. 17, 1959 J. D. HAMILTON, SR Plant Pat. 1,811
RED DELICIOUS APPLE TREE
Filed Jan. 2, 1958
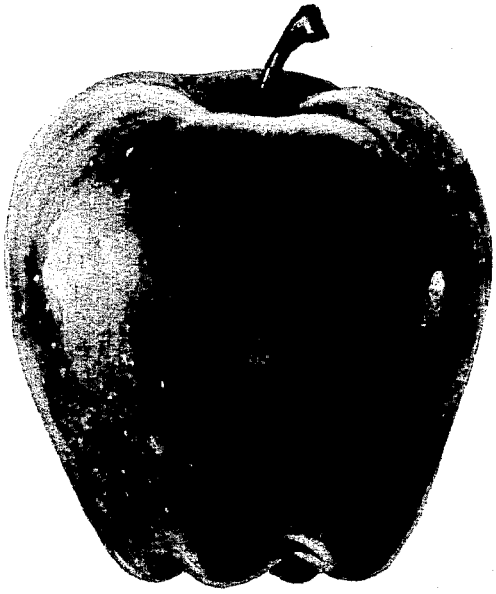
INVENTOR
JOHN D. HAMILTON SR.
BY Hugh N Orr
HIS ATTORNEY United States Patent Office Plant Pat. 1,811
Patented Feb. 17, 1959

1,811

RED DELICIOUS APPLE TREE

John Duncan Hamilton, Sr., Wenatchee, Wash., assignor to The J. D. Hamilton Orchard Company, Incorporated, Wenatchee, Wash., a corporation of Washington Application January 2, 1958, Serial No. 706,884

1 Claim. (Cl. 47—62)

The drawing is a painting showing in true color the ripe fruit which characterizes my new variety of apple tree.

The apple tree of my discovery originated as a sport found by applicant on a parent variety of Red Delicious Apple tree, said sport having been discovered and propagated by applicant on his property located near Chelan, in the State of Washington.

This new variety of Red Delicious Apple tree has been asexually reproduced and propagated by the process of bud-grafting from the original tree discovered by applicant onto young apple tree roots in applicant's orchards near Manson and Chelan, Washington. In the spring, about a year and a half after the grafts were initially made, the first young trees were planted in applicant's orchards. A number of those young trees survived, and in due course bore fruit identical with the parent tree. During succeeding seasons, buds from the young initially grafted trees were grafted onto young apple tree roots as in the initial grafting. The resulting young trees were duly planted and in turn bore fruit. These second generation trees, in turn, have been propagated by bud-grafting to produce a third generation. The trees of the second and third generations have borne fruit substantially identical with that of the original parent tree and the first generation of young trees propagated therefrom. The distinctive characteristics have thus been reproduced through successive generations, and are now accepted as fixed characteristics.

The new variety of Red Delicious Apple tree of my discovery is characterized by a number of distinctive features whereby it is distinguishable from Red Delicious apples of the strains heretofore known and identified. The chief distinguishing characteristic is the color of the fruit. The fruit, as it ripens, becomes a very deep shade of ox-blood red or maroon. The color identified as "Hay's Maroon" shown in Plate XIII in "Color Standards and Nomenclature," published by Robert Ridgway in Washington, D. C., in 1912, most closely approximates the color of the fruit of my new variety of apple tree. The color appears solid over the entire surface of the apple, including the area inside the calyx, which in other Delicious apples is often yellow. This solid color distinguishes it from strains known commercially as the Starking, Red King (Pat. No. 1,411), Hi-Red and Early Red strains, which, so far as applicant is informed, except as indicated, are unpatented. The color is slightly shaded, but not striped. No stripes of any kind occur on the fruit of the apple tree of the present invention, not even the so called "chimera-stripes" of an accidental nature. The type of color and appearance is best described as ranging from "solid" through "shaded" to "blushed" deep-red maroon. This characteristic shade and early coloring distinguishes applicant's Red Delicious strain from the Richared (unpatented) and Royal Red (Pat. No. 1,278) strains.

The fruit of the tree of applicant's invention is further characterized by its early coloring. In this regard, the fruit begins to color, quite early, usually by August 1st and reaches full color about two weeks earlier than other strains of solid color Red Delicious apples.

The fruit has the long, pointed shape typical of the Delicious-type of apple grown in the Chelan-Manson district of Washington. The fruit is "square shouldered" at the stem end, and has the five large pronounced points at the base or calyx end, characteristic of the "Delicious" apple.

The tree of my new variety resembles the ordinary strains of Delicious apple trees with regard to foliage, structure, bark, size, blossoming time and similar characteristics; and is distinguishable therefrom primarily by the early and distinctive coloring of the ripening fruit as above described.

Having thus described my discovery and the propagation of my new variety of plant, I claim:

The new variety of Red Delicious apple tree characterized by its distinctive color and early coloring habit as illustrated and described.

No references cited.